United States Patent [19]

Seare, Jr.

[11] Patent Number: 5,624,674
[45] Date of Patent: Apr. 29, 1997

[54] POROUS PRODUCT MOLD FORM

[76] Inventor: William J. Seare, Jr., 3190 Chula Vista Cir., Salt Lake City, Utah 84121

[21] Appl. No.: 487,964

[22] Filed: Jun. 7, 1995

Related U.S. Application Data

[62] Division of Ser. No. 156,675, Nov. 22, 1993, which is a continuation of Ser. No. 779,387, Oct. 18, 1991, abandoned.

[51] Int. Cl.$^6$ .................................................. A61K 9/00
[52] U.S. Cl. ............................ 424/400; 424/422; 424/423
[58] Field of Search .............................. 424/400, 422, 424/423; 264/126; 623/16

[56] References Cited

U.S. PATENT DOCUMENTS

| | | | |
|---|---|---|---|
| 3,453,194 | 7/1969 | Bennett et al. | 427/551 |
| 3,829,903 | 8/1974 | Stati et al. | 623/2 |
| 3,877,080 | 4/1975 | Olcott | 623/11 |
| 3,890,107 | 6/1975 | White et al. | 428/613 |
| 3,948,254 | 4/1976 | Zaffaroni | 424/423 |
| 3,955,012 | 5/1976 | Okamura et al. | 424/423 |
| 4,021,382 | 5/1977 | Stoy et al. | 260/2.5 |
| 4,082,727 | 4/1978 | Nagata et al. | 525/54.2 |
| 4,413,359 | 11/1983 | Akiyama et al. | 623/11 |
| 4,551,132 | 11/1985 | Paxtor et al. | 604/52 |
| 4,579,555 | 4/1986 | Russo | 604/282 |
| 4,588,624 | 5/1986 | Nygren et al. | 428/34.7 |
| 4,756,862 | 7/1988 | Spector et al. | 264/126 |
| 4,859,712 | 8/1989 | Cox | 521/62 |
| 4,889,744 | 12/1989 | Quaid | 427/2 |
| 4,969,906 | 11/1990 | Kronman | 623/66 |
| 5,030,233 | 7/1991 | Ducheyne | 623/16 |

OTHER PUBLICATIONS

Taylor, S.R., "Effect of Surface Texture on the Soft Tissue Response to Polymer Implants" (1983) pp. 205–227.

Bobyn, J.D. et al. "Effect of Pore Size on the Peel Strength of Attachment of Fibrous Tissue to Porous–Surfaced Implants" (1982) pp. 571–583.

Leidner, Jacob et al., "A Novel Process for the Manufacturing of Porous Graft Process Description and Product Evaluation" (1983) pp. 229–247.

White, R.A., "Replamineform: A New Process for Preparing Porous Ceramic, Metal, and Polymer Prosthetic Materials" (1972) pp. 922–924.

von Recum, Andreas F., "Applications and Failure Modes of Percutaneous Devices: A Review" (1984) pp. 323–335.

Grosse–Siestrup, Christian et al., "Design Criteria for Percutaneous Devices" (1984) pp. 357–381.

Hall, C. William et al., "Some Factors that Influence Prolonged Interfacial Continuity" (1984) pp. 381–393.

Dasse, Kurt A., "Infection of Percutaneous Devices: Prevention, Monitoring and Treatment" (1984) pp. 403–411.

Mentor Corporation "Siltex Low Bleed Gel–Filled Mammary Prosthesis" Brochure (1988).

Brand, Gerhard K., Statement in Disagreement with the Implications and the Validity of Dr. Neil Springarn's Data and Conclusions, (1985).

Piecuch, Joseph F., "Compressive Strength of Implanted Porous Replamineform Hydroxyapatite" (1984) pp. 39–45.

(List continued on next page.)

*Primary Examiner*—Thurman K. Page
*Assistant Examiner*—William E. Benston, Jr.
*Attorney, Agent, or Firm*—Workman Nydegger Seeley

[57] ABSTRACT

The present invention is directed to apparatus and methods for forming open-cell porous mold forms to mold porous devices having substantially continuously interconnected pores. The mold form is made from selected material comprising particles having predetermined sizes and shapes which is capable of forming a stable mold form under selected conditions. The particles are treated such that the particles are manipulable into a mass of continuously interconnected particles defining continuously interconnected pores and connecting interstices within the mass. The formed mass is made into a predetermined shape and solidified to form a mold form.

21 Claims, 8 Drawing Sheets

OTHER PUBLICATIONS

Brand, K.G., "Histological Study in Mice on Capsule Formation Around Polyurethane–Coated Silicone Implants" (1983).

Brand, K. Gerhard, Correspondence to H. Markham re histopathological study (1982).

Plastic & Reconstructive Surgery Div., "CooperSurgical" brochure.

Markham, Jacqueline "Firm Capsules and Memes" Paper.

POROUS PRODUCT MOLD FORM

This application is a divisional of application U.S. Ser. No. 08/156,675, filed Nov. 22, 1993, which is a continuation of U.S. application Ser. No. 07/779,387, filed Oct. 18, 1991, now abandoned.

BACKGROUND OF THE INVENTION

The present invention relates to a device, at least a portion of which is porous, for use as a prosthesis, treatment implement, and other utility, and a process of fabricating such device.

The applications and uses of synthetic biocompatible implements and devices adapted for implantation or installation in or on a human body have dramatically increased in recent years. Such implements and devices include soft tissue implants for use, for example, in breast augmentation, chin, nose, ear and other body part reconstruction and the like, nerve cuffs and scaffolds, lymphedema shunts, percutaneous skin and blood access devices, insulin cell producing implants and other cell sequestrating cage devices, artificial tendon and ligament and tendon and ligament repair prostheses, artificial heart and vascular prostheses, burn dressings, and drug infusing, releasing or delivery devices.

Oftentimes, devices of the type described above fail due to problems at the implant-tissue interface. As early as 1970, Homsey, recognized that if the implant size is in the order of centimeters, a "fibrocartilaginous" membrane or capsule isolates the implant from normal tissue. If the implant is perforated so that the interstices (pores and pore interconnections) are of the order of 1 mm or less, the implant becomes woven with the tissue, rather than encapsulated as above (Homsey, C. A., 1970, *J. Biomed. Mater. Res.*, 4:341–356). Smooth-walled silicone breast implants fail in the order of 40–60 percent due to this thick "fibrocartilaginous" membrane (capsule) which forms around the implant creating a hard, inelastic, and often painful feeling implant. This fibrous capsule also creates other problems around implants in general because it is composed mainly of dense compacted collagen, and fibroblasts, with little or no vascularity. This leads to isolation of the implant, the implant-capsule interface, and the capsule itself from the nutrient, metabolic, and cellular advantages of good blood supply, making the implant site more prone to infection, and the infections less amenable to treatment by natural resistance mechanisms and/or blood borne antibiotics.

Porous devices known under the trade names Ivalon Sponge (polyvinylchloride) and Ashley breast prosthesis (polyurethane) were created to allow tissue ingrowth into the pores within the implant. These devices were totally porous, sponge-like devices which didn't limit the tissue ingrowth into the pores or limit implant access to bodily fluids and, with nothing to stop or control such ingrowth or fluid access, poor quality ingrown tissue, with interior calcification and hardening, resulted. Such hardening is not only uncomfortable to the recipient but also unnatural in appearance and function.

In an attempt to solve some of the above problems, at least with breast prosthesis, polyurethane foam covered silicone rubber breast protheses, both with and without a silicone shell surrounding gel, were developed, but with mixed results. For the prostheses using a silicone shell, the polyurethane foam was mechanically fixed to the shell with silicone adhesive. However, the interface between the foam and shell was weak and oftentimes resulted in delamination, sometimes with leakage of the silicone gel into the surrounding tissue. For the prostheses not utilizing a silicone shell, the gel would typically leak or "bleed" through the polyurethane cover into the surrounding tissue. Such "contamination" of the surrounding tissue with the gel caused local inflammation and gel migration to distant organs. Also, because of the three-dimensional interlocking nature of the pores within the polyurethane foam, the relatively inelastic nature of the polyurethane, and the large ratio of ingrown tissue compared to the amount of material in the foam, a "Chinese handcuff" type situation (ingrown tissue locked with foam) was created with the tissue, making it very difficult to remove or change the prostheses. Further, polyurethanes, as a class, are biologically unstable and will chemically degrade, giving rise to structure breakdown, sometimes with severe inflammation. A recent concern with such chemical degradation is the potential for release of toluene diamine (TDA), a chemical which, even in small amounts, is known to cause cancer in laboratory animals.

Previous approaches to forming porous materials (for implants or other uses) have typically included use of bubble-forming technology, sintering of metal or polymer particles into a partially fused body, expansion of polymer melts or solutions (such as used to produce Gortex), processing fibers to produce fabric felts, velours, meshes or weaves, and replicating or duplicating the microstructure of carbonate animal skeletal material. See, for example, White, R. A., Weber, J. N. and White, E. W., "Replanineform: A New Process for Preparing Porous Ceramic, Metal, and Polymer Prosthetic Materials," *Science*, Vol 176, pp 922–924; U.S. Pat. No. 3,890,107; Leidner, J. et al., "A Novel Process for the Manufacturing of Porous Grafts: Process Description and Product Evaluation," *Journal of Biomedical Materials Research*, Vol. 17, pp. 229–247 (1983). Among the problems of using bubble technology to produce porous materials is the difficulty of separately controlling pore size, pore shape, and pore interconnections. Also, the resulting pores typically include sharp edges and terminations which can cause accelerated inflammation and thus problems and/or discomfort when implanted. The sintering and polymer expansion approaches are limited to the use of only certain kinds of materials, typically metals for sintering and polytetrafluoroethylene for polymer expansion, and these may not be materials having the desired flexibility, resiliency, biocompatibility, or the like. The processing of fibers is limited because only materials which can be made into fibers can be used, and the resulting structure is basically two-dimensional. The replication of carbonate animal skeletal material, although suitable for some uses, requires milling of the material to the desired size and shape, and again the pore size and shape cannot be controlled.

Two recently issued patents, U.S. Pat. Nos. 4,859,712 and 4,889,744, disclose the use of dissolvable particles initially placed on uncured silicone, curing the silicone, and then dissolving the particles to yield a silicone product having a purportedly open-cell porous surface. The particles mentioned in both patents as the preferred solid soluble particles are crystalline sodium chloride (salt) and no other exemplary particles are identified. A number of problems or difficulties are present with the methods disclosed in the two patents including the difficulty of obtaining a completely open-cell structure since the salt particles are simply placed in the surface of the implant before curing, and then the implant is cured and the salt particles dissolved. Since many of the particles will not touch, a mostly closed-cell section is produced except at the surface layer. With this technique, it is also difficult, if not impossible, to premold the solid particles into predetermined desired shapes (since salt particles do not hold together and therefore cannot be molded), and the depth of the porous portion, and the size and shape of the structural interconnections surrounding the individual open cells cannot be controlled (since salt crystals can only be pressed into contact with one another but do not inherently stick together).

Since the treatment possible with the approaches disclosed in the above two patents is only at the surface and doesn't extend in a true three-dimensional direction, the fibrous capsule created after implantation has essentially the same thickness and density as with a smooth surfaced implant. A true three-dimensional unitary porous silicone rubber prosthesis has not been available until the technology of the present invention was developed.

SUMMARY OF THE INVENTION

It is an object of the invention to provide a new and improved open-cell product, and process for constructing same.

It is another object of the invention to provide such a process in which the degree of porous versus nonporous portions of the product can be separately controlled.

It is a further object of the invention to provide such a process in which the size and shape of pores of the open-cell product can be predetermined and controlled.

It is an additional object of the invention to provide such a process in which the size and shape of the entire porous portion of a partially porous product can be controlled.

It is also an object of the present invention to provide a process and resulting product in which the porous portion and the non-porous portion of the product are made in a unitary fashion, without an interface between the two portions.

It is still a further object of the invention to provide such a process and resulting product which, when used as a body implant, serves to reduce or eliminate calcification, hardening and fibrous capsular formation, and to promote new loose tissue and new vessel ingrowth to thereby increase recipient acceptance of the prosthesis.

. It is still another object of the invention to provide such a process and product in which the resulting pores of the porous part of the product are free of sharp edges and terminations to thus increase acceptance by a patient when implanted or applied to a body part or organ.

The above and other objects of the invention are realized in a specific illustrative method of preparing a device of a selected material to have pores and pore interconnections of predetermined sizes and shapes. The method includes the steps of forming a selectively removable open-cell porous mold form (SRO-CPMF) comprising particles which adhere together and have sizes and shapes corresponding to the desired pore sizes and shapes, and particle connections which bind the particles together in the desired form, where the particle connections correspond to the desired sizes and shapes of the pore interconnections. The vacancies or voids between the particles of the mold form are then filled with the selected material, the material converted to its solid form, for example by polymerization, and the mold form is removed, for example by dissolution, to thereby leave the selected material in place. The resulting porous device includes pores and pore interconnections corresponding in size and shape to the particles and particle connections respectively, as desired.

Examples of materials suitable for the resulting porous device include polymers, metals, metal alloys, ceramics, biological derivatives, and combinations thereof, in solid or fiber form. Examples of materials suitable as mold material for forming the SRO-CPMF include sugar, thermoplastic polymers such as waxes, paraffin, polyethylene, nylon, polycarbonate, or polystyrene in naturally available particles or processed into specific sizes, shapes, molded forms, spheres or fibers, salt or other particles which cannot be made to inherently stick together coated with sugar, and certain drug crystals such as gentamycin, tetracycline, or cephalosporins. In general, any dissolvable, burnable, meltable, or otherwise removable particle which can be made to stick together could be used.

Many particles are available from manufacturers in a wide range of sizes (or shapes) such as, for example, polystyrene spheres. Where specific sizes, shapes or forms of a material are not available, they may be custom formed. In the sugar example, the sugar may be heated with corn syrup and cooked to cause the mixture to polymerize and form hardtack. While still hot and in its liquid form, this mixture may be poured into molds, extruded into fibers or injection molded into specific shapes, or cooled and crushed into sized particles. Similarly, any thermoplastic polymer may be processed for specific sizes or shapes, any of which could be used for an SRO-CPMF.

With the method of the present invention, the surface terminations of the porous portion of a structure are generally smooth and rounded, unlike terminations of porous portions constructed with prior art methods. The pores of such porous sections may also vary in size not only from pore to pore, but also from one portion of the pore section to another portion. Such porous sections may also be formed to extend to a selected depth in the structure, or all the way through the structure if that is desired.

DESCRIPTION OF THE DRAWINGS

The above and other objects, features and advantages of the invention will become apparent from a consideration of the following detailed description presented in connection with the accompanying drawings in which.

DETAILED DESCRIPTION

In carrying out the process of constructing porous or partially porous products in accordance with the present invention, a first step is simply to select the mold material for use in forming the selectively removable open-celled porous mold form (SRO-CPMF) from which the final product will be molded. Such mold material, advantageously, is readily available, inexpensive, and resistant to dissolution by the liquid form (or the dissolved or dispersion form) of final product material. Also, the mold material should be available in selectively sized and shaped particles which may readily adhere together (or be made to adhere together) to thereby assure a continuous and entire open-cell product when the mold material is removed or dissolved away. Finally, the mold material, when in the mold form, should be readily removable without significantly altering the final product (or product material). This removal may be by dissolution by some solvent which does not significantly dissolve the final product material. Alternatively, the mold material may be melted (or burned) out of the final product material if the melting point (or burning point) of the mold material is below that of the final product material.

The final product material likewise would be selected to have the desired characteristics, for example, flexible and resilient for some applications in which case silicone rubber might be selected, and rigid in other applications in which case a polyester resin, epoxy resin, metal or metal alloy or ceramic may be selected.

In the first example to be discussed, a partially porous device will be described, as well as a method of controlling the location of porous and nonporous sections. In this illustrative embodiment, sugar is selected as the mold material or SRO-CPMF, and silicone rubber is selected as the final product material.

Sugar may be obtained with fairly uniform particle size and faceted crystal shapes and, if even greater uniformity of size is desired, then the particle size may be selected using standard screen-sizing techniques.

Once the desired particle size and size distribution for the sugar mold material are obtained, the sugar particles are mixed with de-ionized or purified water in a volume ratio of from 8 to 25 parts sugar to 1 part water. If a higher percentage of porosity in the final product is desired, then more water is added to the mixture to produce greater surface contact and fusing of the sugar particles, and this, in turn, produces more numerous and larger pore interconnections. A lower percentage of porosity in the final product is achieved by using less water, thus resulting in less contact and more space between the SRO-CPMF particles. If a larger pore size in the final product is desired, a larger particle size is chosen. Conversely, if a smaller pore size in the final product is desired, a smaller particle size is chosen.

Figure 1:
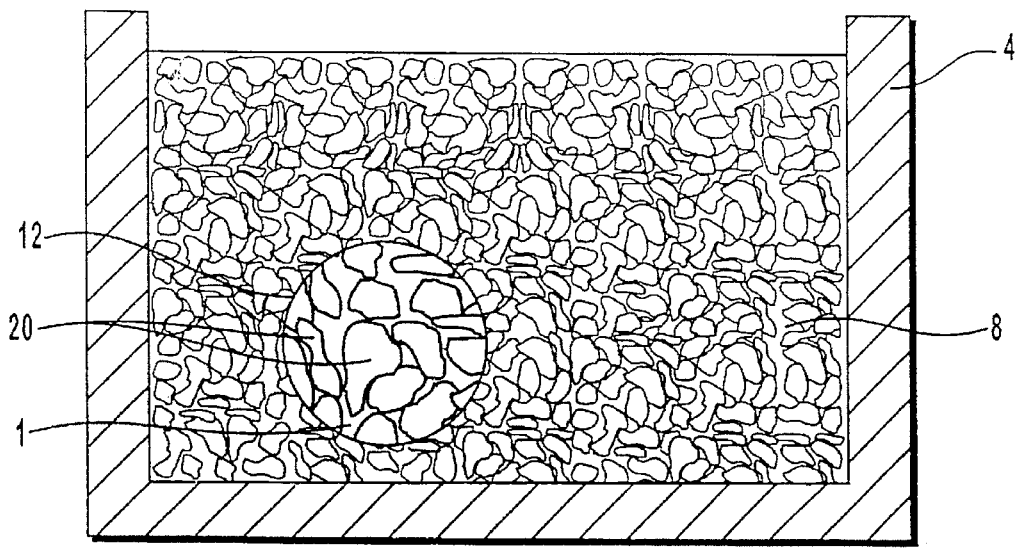
FIG. 1 shows a side, cross-sectional view of a container in which is deposited sugar mold material for making a porous material product, and an enlarged view of a portion of a solidified sugar mass, in accordance with the principles of the present invention.

The sugar and water are thoroughly mixed until all of the sugar particles have been contacted by the water and to some extent partially dissolved resulting in a saturated sugar solution (no more dissolution can take place). When the desired consistency is reached and the mixture is stabilized, the resulting moist semi-solid mass (moldable mass) may be molded into any desired shape by placing it in a pre-shaped mold and allowing it to solidify into the mold form, i.e., allowing or causing the water within the mold form to evaporate and the sugar in solution to recrystallize and precipitate on and between the sugar particles. FIG. 1 shows a cross-sectional view of a conventional cylindrically-shaped container 4 in which is deposited a moistened mass of sugar 8. Section 12 of the sugar mass represents a magnified portion of the sugar granules 15, with the voids 16 between the granules.

Solidification of the moldable mass into the SRO-CPMF may be accelerated by supplying dry air (which may be heated) to the mass, for example. Freezing, freeze drying or vacuum desiccation, with or without added heat, may also be utilized to cause the mass to solidify. Enlarged view 12 of the SRO-CPMF shows the sugar granules or particles 20 fused together, leaving voids 16 between the particles.

Figure 2A:
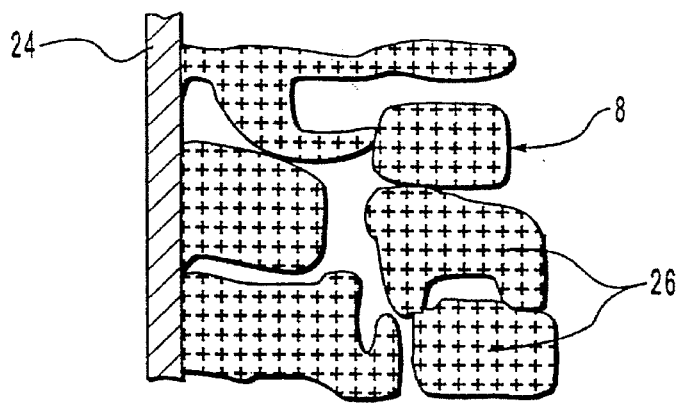
FIGS. 2A, 2B and 2C show fragmented, cross-sectional views of a sugar mass in a container, and resulting final porous products, respectively.

After solidification, the sugar mold form may either be left in place in the container 4 (FIG. 1) or removed from the container 4 (as will be the case in the FIG. 3 description hereafter), depending on the nature of the final product desired. For example, by leaving the sugar mold form in the container 4, the mass will maintain contact with and adhere to the container walls 24 (FIG. 2A) so that supply of the final product material to the mold form (to be described momentarily) will result in a porous surface 28 in the final product (FIG. 2B), with the surface pores 30 being formed by the sugar particles 26 of the mold form (FIG. 2A) in contact with the container wall 24. On the other hand, if the sugar mold form 8 is removed from the container (or the adherent surface at the container wall is eliminated) and the final product then supplied to the mass, for example, as it is held in a larger container 38 (FIG. 3A), the surface exterior 40 (FIG. 3B) of the final product (covering the sugar mold form) will not have pores. FIG. 3B shows this nonporous surface area and section 40, with a porous interior 42; the thickness of this nonporous section 40 will depend upon the quantity of final product material applied to the outside of the mold form.

Another illustrative method for forming the SRO-CPMF involves placing pure sugar particles of the desired size in a metal container and then heating the particles slowly to slightly below or just at the sugar melting point. While this is being done, the sugar particles are compressed and forced to contact each other, and then the mass is allowed to cool. The more the sugar particles are compressed together, the more numerous and larger will be the size of the particle connections, the more dense will be the SRO-CPMF, and the greater will be the percentage porosity of the porous portion of the final product, and vice versa. After cooling, the mold form may either be removed from the container or left in contact with the container as discussed above.

After the sugar mold form is completed, a medical grade silicone rubber is catalyzed, mixed and de-bubbled in a conventional manner to achieve a liquid state and to prepare the silicone rubber for subsequent polymerization, i.e., conversion from liquid to solid state. The prepared, catalyzed silicone rubber is then forced into and through the interstices or pores of the sugar mold form for example by pressure application to the silicone rubber, vacuum application to the mold form, gravity flow, mechanical agitation or a combination of these techniques, all of which are well-known. The thickness of the porous portion of the final product can be less than or equal to the thickness of the SRO-CPMF. This can be specifically controlled by controlling the depth of penetration into the SRO-CPMF of the liquid form of the final product material. If the liquid is forced to completely penetrate the mold form, the specific thickness of the SRO-CPMF itself can be used to control the thickness of the porous portion of the device.

Following supply of liquid silicone rubber to the mold form, the silicone rubber is allowed (or caused) to polymerize after which the sugar mold form is dissolved by a suitable solvent (in this case de-ionized water) and agitation. What is left after this step is the desired silicone rubber final product. A number of washings may be required to completely remove all of the residual sugar and ultrasonic water baths or other agitation is especially effective to do this. Also, hot de-ionized water or steam rinses could be utilized, after which the final product would be dried.

Figure 3A:
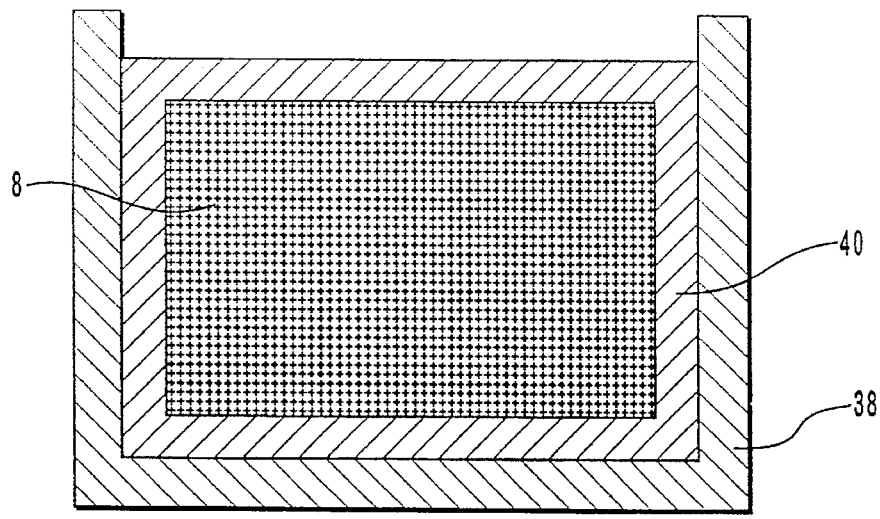
FIGS. 3A and 3B show an elevational, cross-sectional view of a container with sugar mold material and final product material, and an elevational, cross-sectional and fragmented view of the final product, respectively.

If the combined structure of the SRO-CPMF and final product material was developed by removing the mold form from the container before applying the final product material to the mold form, FIG. 3A then a coating of final product material would surround the mold form resulting in a nonporous covering 40 so that there would be no access for the solvent to reach and dissolve the mold form 8 (FIG. 3A). In this case, a small portion of the final product material would be removed at a surface location to allow access of the water solution to the interior. Alternately, needle penetration of the solid product material 40 could provide the desired access for the water solution, and removal of the dissolved sugar.

The thickness and shape of a nonporous surface portion of a final product can be readily adjusted by standard molding or injection molding die techniques such as by selecting an appropriately sized and shaped container in which to place the mold form and then filling the container or mold with the unpolymerized silicone rubber. If the SRO-CPMF occupies only a small volume of the container, then the thickness of the non-porous portion of the final product will be great. The size and shape of the non-porous portion of the final product is determined by the size and shape of the container in which the mold form is placed less the size and shape of the mold form placed in the container.

The shape and the amount of the porous portion of the final product will be determined by the shape and the portion of the mold form filled with the final product material. Any portion of the mold form not filled with the final product material will result in a void 142 in the final product (see FIGS. 8C and 8D). The position of the porous portion relative to the non-porous portion of the final product will be determined by the placement of the mold form within the mold.

Except in a case to be described later (where a gas is forced through the mold form), one portion of the surface of the final product material will be non-porous. This portion corresponds to the location of introduction of the liquid form of the final product material into the mold form. By controlling the adherence of the mold form to the container or mold surfaces, the completeness of penetration of the liquid form into the mold form, and by controlling which surface area and the size of that surface area at which the liquid form of the final product material is introduced into the mold form, the location of the opened-cell surfaces and the location of the non-porous surfaces may be controlled. For example, a product made into a sheet may be entirely porous on the lower surface and non-porous on the upper surface. As an example using the adherent container wall 4 to the mold form 8 in FIG. 1, this would be done by introducing the final product material to completely penetrate the mold form 8 on its entire upper surface, keeping the lower surface of the mold form adherent to the container walls. Alternatively, the final product material could be applied to penetrate only partway into the mold form. Either example results in a partially porous final product (FIG. 2C) with a nonporous upper surface 32, and a porous portion 34, with porous surfaces on the sides and bottom of the porous portion 34. However, if the final product material is introduced from the side, with an otherwise adherent (to all the container walls) mold form within the rest of the mold, the upper and lower surfaces of the sheet, as well as the sides where the liquid is not introduced will be porous. In this manner, the surfaces of the porous portions versus non-porous surface portions of the device can be controlled.

The final silicone rubber product which is at least partially porous is cured (polymerized), for example, in a drying oven for 15 minutes to 1 hour at a temperature ranging between 275 degrees F. and 425 degrees F., depending upon the specific silicone rubber used. The final product can be further formed or sculpted by cutting or adding to the product or by gluing other solid or porous silicone rubber parts or materials. However, the advantage of the method of the present invention is that rarely would one need to cut, glue, sculpt or add to the final product, since the variables between the porous and non-porous portions can be separately controlled. Cutting, gluing and sculpting, etc. also add interfaces and irregularities, stress risers and contour defects. In the method of the present invention, the porous and the non-porous portions of the device can be unitary, without interfaces, defects or contour irregularities. Standard packaging and sterilization procedures can then be performed if desired.

With the above-described process for forming open-cell porous products, complex shapes, forms and sizes may be readily fabricated. Also, there is no limitation as to the location of the porous portions of the product as there is with prior art methods.

A second example of the present invention will now be described in which the pore size of the porous portion of the final product will vary. Initially, small particles of sugar (e.g., 50–75μ) are placed in a container to a depth of, for example, 0.2 mm. Another size range of particles of sugar (e.g., 100–150μ) are then placed to another specified depth, say 0.3 mm, over the first layer. This is continued until a final layer is added, say 200–300μ particles size, for a depth of 0.6 mm. The SRO-CPMF particles in the container are then made to stick together either by adding a saturated solution of sugar to all of the particles and draining it off the bottom by vacuum, or by exposing the container and graduated sized particles to near 100 percent humidity for 15 minutes to 4 hours, and then allowing the SRO-CPMF to dry (harden). Alternatively, the particles may be heated just to the melting point, compacted and cooled as described previously. The SRO-CPMF is then filled with the liquid form of the final product material as previously described-here silicone rubber. The resultant product is a partially porous device where the porosity varies selectively or continuously as desired, from one area to another. This is illustrated in FIG. 3B where the pore size varies from smaller to larger in the direction away from the nonporous section 40.

With the above-described method, many useful devices have been produced, such as vascular graft prostheses made from medical grade silicone rubber, Biomer, and Biolon (medical grade polyurethanes). The blood-facing surface of vascular devices have been constructed as above with pore sizes of 25µ, 50µ, 75µ and 100µ. The porosity through the rest of the product may range from 30µ to 300µ, with a wall thickness ½ to 2 mm. Cell cultures of endothelial and smooth muscle cells have been grown on the blood-facing surface of the device, where the porosity assists the attachment and, subsequently during implantation, the porosity adds to the nutrition of these cells during and after the ingrowth of tissue and neovascularity.

With larger pore sizes (50µ to 100µ) on the blood-facing surface of vascular grafts, pre-clotting the graft is necessary. After tissue ingrowth, the neovascularity may support neointimal cellular regeneration on the blood-facing surface of the device with or without cell culture seeding.

The vascular prostheses described above may be implanted into subcutaneous or intra-muscular positions. After the prosthesis walls become filled with tissue (from several minutes [pre-clotting] to several days [cell seeding] to several weeks [tissue ingrowth] depending on the type of tissue desired), the prosthesis may be removed from its position and transplanted as a composite (composed of two types of material—tissue and polymer) graft into the recipient site, in this case a blood vessel. In this way, a vascular graft composed of tissue (as well as polymer) can be used as a live autogenous graft without creating the donor-site morbidity of sacrificing a blood vessel. In a similar fashion, many types of tissue may be transplanted including bone marrow, liver, pancreas, collagen, or neovascularity or any tissue or cell culture which can be made to grow into the porosity of the implant.

A third example of the invention involves the use of fibers disposed within, or within and extending from, the porous section of the final product, for reinforcing or changing the characteristics of the porosity of the final product. The construction of such a final product will now be described.

Figure 4:
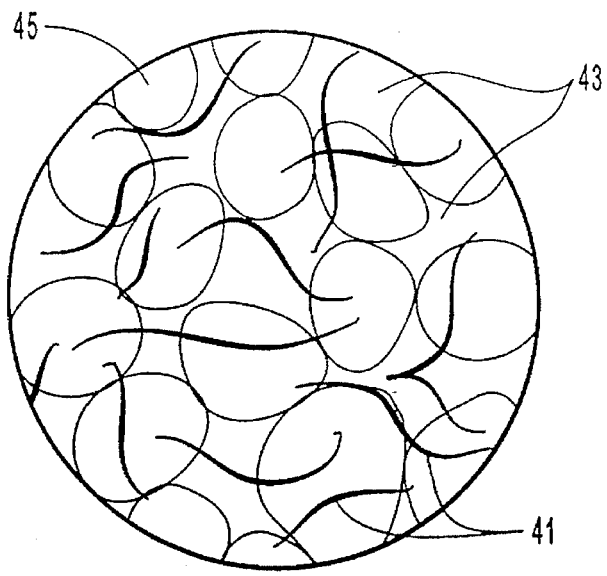
FIG. 4 shows an enlarged cross-sectional, fragmented view of final product material which includes fiber fragments, in accordance with the present invention.

After mixing the sugar moldable mass, as in the first example (see FIG. 1), commercially available fiberglass or carbon graphite fibers are cut to the desired length, for example, 1 cm., and mixed randomly with the moldable mass. The moldable mass is then placed in a container as before and allowed to solidify, forming the SRO-CPMF. For any given fiber, part of the fiber is within the sugar, either resting on a particle which has been partially dissolved and subsequently has some additional sugar deposited and recrystallized on its surface, or within sugar deposited and solidified at the particle surface and/or the particle connection. Also for any given fiber, part of the fiber may not be in contact with sugar but rather simply extend into the voids of the SRO-CPMF. If a flexible reinforced porous section is desired in the final product, final product material, such as silicone rubber is selected. If a rigid final product is desired, polyester or epoxy resin, is introduced into the voids of the SRO-CPMF as previously described. The part of the fiber which is exposed within the void becomes coated and incorporated within the matrix of the final product material. The sugar of the SRO-CPMF is then dissolved so that that part of the fiber 41 (FIG. 4) within the sugar becomes exposed within voids 43 of the final device 45—these exposed fibers can be ingrown by and fixed to tissue after implantation.

The proportion of fibers mixed into the SRO-CPMF may be varied greatly depending on the stickiness availed to the particles within the SRO-CPMF (either inherently or by the binding medium used), and the wetability, diameter, and stiffness of the fiber itself. If the fiber to moldable mass particle ratio becomes too great, the moldable mass particles become non-adherent to each other and the interconnecting open-celled nature of the SRO-CPMF breaks down, i.e., it can no longer be used as a porous mold form.

The length of the fibers used can also vary greatly. They can be oriented, pre-stretched or pre-woven, and placed within the container before the introduction of the moldable mass to thereby fix their position, orientation, etc. within the SRO-CPMF, and thus within the final product. The fibers can also be disposed to extend out of the SRO-CPMF, and thus out of the voids of the final product and into non-porous portions or outside the final product itself.

Similarly, a medical grade Dacron mesh (hole size about 1 mm) may be formed into a cylinder, for example, having a diameter about 2 mm less than the diameter of the inside walls of a container in which it is placed. After placement in the container, a moldable mass is placed in the container about and within the mesh cylinder, compacted, and allowed to solidify. This results in the mesh resting 1 mm from the container wall within its circumference and within the SRO-CPMF, with sugar particles and sugar particle connections being in continuity on each side and through the mesh. The SRO-CPMF is then removed and placed into another container, for example about 1 mm larger in diameter than the SRO-CPMF. Final product material, such as catalyzed liquid silicone rubber, is then forced about and into the SRO-CPMF to a depth of, for example, 2 mm and allowed to solidify (polymerize). The SRO-CPMF is then dissolved as described above and the ends of the tube are cut off. The resulting prosthesis is inverted (turned inside out) yielding a device which is smooth and non-porous to a depth of ½ mm on the inside, with a porous section to a depth of 2 mm on the outside. The central portion of the porous section is reinforced circumferentially by Dacron mesh, but with the porous section positioned on both sides and continuous through the mesh.

The device described above has been used a percutaneous cuff prosthesis for artificial heart drive lines; it is slid over and glued to the lines at their exit point through the skin and this allows tissue ingrowth and fixation at and below the skin. Similar reinforced and fiber-modified porous prostheses have been made as vascular prostheses from medical grade blood compatible polyurethanes.

In the earlier example in which the sugar SRO-CPMF mold material was removed from the container before applying the liquid silicone rubber, one of the options for the final product was to make it porous on the inside and nonporous on the outside (FIGS. 3A and 3B). However, in many biomaterial uses, it is desirable to have a porous section on the outside and a nonporous section on the inside, in various shapes and ratios. An example of the use for such a final product is a dorsal nasal augmentation implant, and the process for fabricating such a final product (as well as similar final products) will next be described.

The first step in the process is to form a positive model in the exact size and shape of the desired final implant, made from substantially any material although the clay-like thermoplastic material known as Sculpey Modeling Compound has proven to be most satisfactory. Such material is formed and sculpted by hand or with molding tools into the desired shape and then solidified by heating the material to 300 degrees F. for about 15 to 20 minutes. A single positive model may be used to fabricate a number of SRO-CPMF molds and therefore a number of final products, and the thickness, position and shape of the porous versus nonporous sections may be controlled.

Figure 5A:
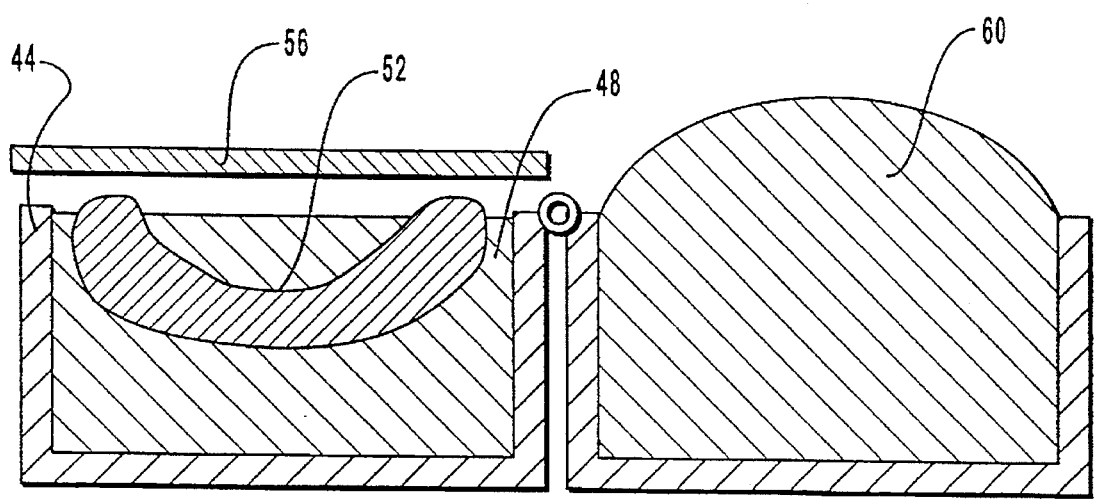
FIGS. 5A, 5B, 5C and 5D show elevational, cross-sectional views of a mold container shown in the open position, two closed positions, suitable for use in accordance with the process of the present invention, and a final product, respectively.
Figure 5B:
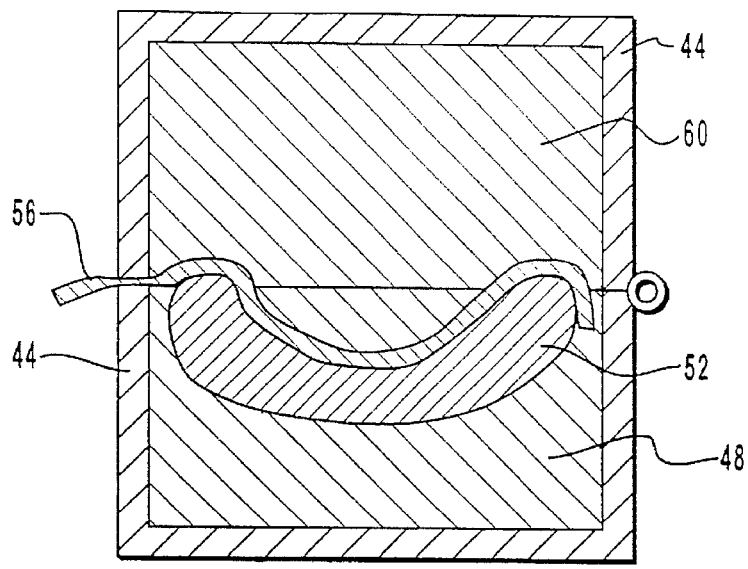

The positive model is then placed in a hinged rectangular container 44 made of polyethylene (FIG. 5A), in one half of which is placed the mold material for the SRO-CPMF 48 such as sugar moldable mass. The positive model 52 (in this case a nose implant) is then pressed partway into the mold material 48 so that only its top (concave) surface is exposed. A thin layer of polyethylene sheeting or similar nonadhering material 56 is then placed over the mold material 48 and positive model 52. The other half of the hinged container is then filled (or overfilled) with sugar moldable mass 60 after which the container is closed, as shown in FIG. 5B, so that the moldable mass 60 is forced tightly over the sheeting 56 to conform to the shape of the exposed surface of the positive model 52. The mold material 48 and 60 is then allowed to dry (solidify) and the two halves of the hinged container 44 are reopened to allow removal of the sheeting 56 and the positive model 52 to leave the SRO-CPMF 48 and 60 in place in the container. Alternatively, the hinged container 144 could be first carefully opened, and the sheeting 56 and model 52 removed to allow drying of the moldable mass into the SRO-CPMF.

Figure 5C:
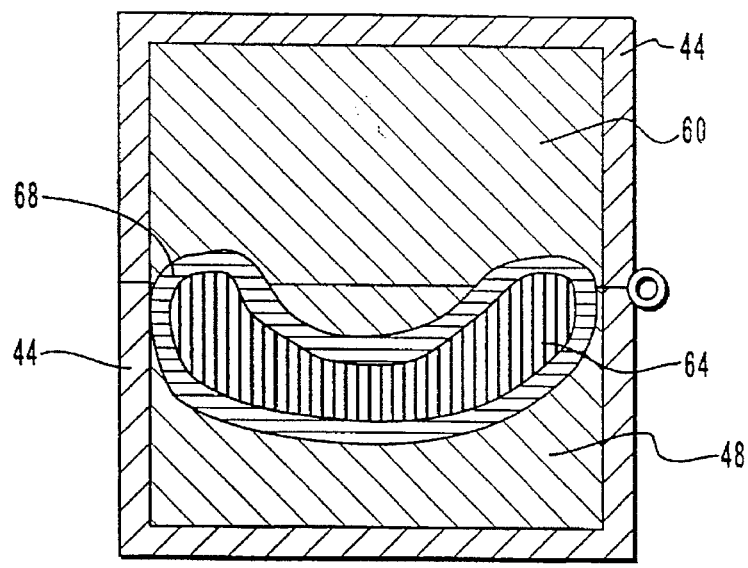
Figure 5D:
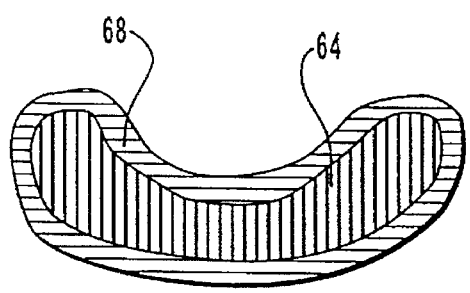

A medical grade elastomer such as RTV silicone rubber is then forced into the mold form 48 and 60 to a depth equal to the desired thickness of the porous surface area of the final product. Silicone rubber is also placed in the void in the polym-mold material 48 and 60 left by the positive model 52 and then the container 44 is again closed, as shown in FIG. 5C. The silicone rubber is allowed to polymerize while in the mold 48 and 60 of FIG. 5C after which the container 44 is opened, the mold form dissolved, and the final product implant removed to form a silicone rubber nasal implant having a solid interior 64 and a porous outside surface area 68 in FIG. 5D.

In addition to the above-described process for forming a nasal implant or similar final product, conventional injection molding techniques are also effective in forming with the SRO-CPMF, by sintering sugar or other removable materials with heat and pressure in dies and molds in the desired shapes and with the desired voids or models to create the voids. The final product material, i.e., silicone rubber, is then pressure injected into the voids and into the mold form to the desired depth, with the same molds or dies used in forming the mold form or other dies or molds as needed. The resultant device using either process is a partially porous final product in which the locations and thicknesses of the porous section and the solid nonporous core and/or voids have been effectively controlled. A more viscous mass can be made by using corn syrup rather than water as the sugar binding-dissolution medium and this will provide larger particle contacting in the mold form and therefore larger pore interconnections in the final product. The viscosity of the final product material will also affect the porosity of the final product when solidified. If a thick viscous silicone rubber solution is used, for example, then larger pores will be produced in the final silicone rubber product since the more viscous unpolymerized silicone rubber will contact the SRO-CPMF particles over less surface area to effect incomplete surface molding. Also the pores will be smoother and more rounded as will be the pore interconnections.

Figure 6:
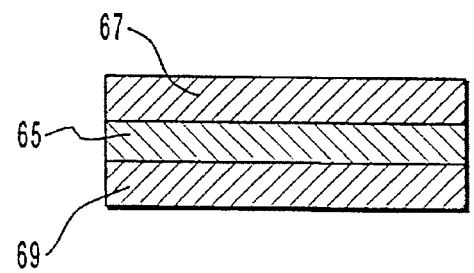
FIG. 6 shows a side, cross-sectional view of a product having top and bottom porous sections with a middle, nonporous section.

A doubly porous membrane (porous on each side but separated by an impermeable membrane) can be formed as in the steps just described for the nose implant. Here, the process is essentially the same except the positive model 52 (FIG. 5A and 5B) is eliminated; rather, the two halves of the hinged container are closed over the nonadherent sheeting 56, causing the two opposing surfaces of the moldable mass material 48 and 60 (separated by sheeting 56) to conform to each other. The hinged container 44 is then opened, the sheeting 56 removed, and the mold material 48 and 60 allowed to solidify. The final product material is then placed between the two mold material 48 and 60 and then forced thereinto to the depth desired. Upon curing, a final product as in FIG. 6 of a nonporous membrane 65 with two porous surfaces 67 and 69 are produced. The thickness of the non-porous membrane 65 can be controlled by controlling the thickness of the non-adherent sheeting 56 and the degree to which the two opposing surfaces of the SRO-CPMF are forced together. Complex shapes and implements such as tubes and external surfacing for use in artificial hearts and vessels, porous on one or both sides, have been created in a similar manner utilizing silicone and biocompatible polyurethanes.

Another example of a partially porous device made in accordance with the present invention is a breast implant. The beginning positive solid model, for example, polymethylmethacrylate formed with the desired curvatures and dimensions by machining or other suitable forming techniques, is polished and cleaned so that there is no contamination. Then, as with the formation of the nose-bridge implant, a hinged rectangular container 74 (FIG. 7A) somewhat larger than the positive model 82 is filled with the sugar moldable mass 78 and 80 on each side. The polymethylmethacrylate breast implant model 82 is then pressed partway into the moldable material 78, in one half of the container, so that the upper convex surface of the model is exposed. A thin layer of polyethylene sheeting 86 or other thin, non-adhering sheeting material is then placed over the model and the container 74 is closed tightly over the polyethylene sheeting. The moldable mass 78 and 80 is then allowed or caused to solidify as in the previous examples after which the container 74 is opened and the model 82 and the sheeting 86 removed. A medical grade elastomer 90 (FIG. 7B) is then forced into the SRO-CPMF 78 and 80 to a depth equal to the desired thickness of the porous coating of the resulting final product (any excess is drained off depending on the desired thickness of the nonporous portion), after which the parts of the container 74 are again closed tightly and the elastomer is allowed to polymerize. Additional coats of polymer may be applied to the inside of the SRO-CPMF to build up the nonporous shell thickness of the final product to the desired specifications. (A small hole must be left at some location if introduction of additional liquid form of the final product material into the void and onto and into the surfaces of the mold forms 78 and 80 created by model 82, as will be discussed momentarily, is needed.) The layers may be added before final polymerization, so that there may be no interfaces between the porous and nonporous portions or between the nonporous portions of the device.

The container 74 is again opened and the mold forms 78 and 80 are dissolved from the elastomer 90 by multiple washings, etc. The resultant breast implant device seen in FIG. 7C is partially porous, having a predetermined thickness of porosity on the entire outside surface 94, a next interior layer of non-porous elastomer 98, and an interior void 102. The void may be left or later filled with some type of material to provide a breast implant with the desired feel, malleability and function. For example, the void 102 might be filled with a normal saline solution to yield a saline-filled breast prosthesis. The void 102 might also be filled or partially filled with a semi-solid such as a partially cross-linked silicone elastomer creating a silicone gel-filled implant. Finally, the void 102 could be filled with a catalyzed unpolymerized elastomer and allowed to polymerize and fully cross-link to create a rubbery, nonporous form with a porous covering. For some applications, it might be necessary to leave the void or to fill the void with a gas such as air.

Another specific illustrative embodiment of the method of the present invention for making a breast implant involves use of a two-part polyethylene mold 114 (FIG. 8A) defining a cavity 118 having an oval cross-section, into which is placed the sugar moldable mass 122. Also disposed to extend from the mold form 122 through an opening in the mold 114 is a handle 126 made of stainless steel or other stable, corrosive-resistant material. After forming, the SRO-CPMF 122 with attached handle 126 is removed from the mold 114.

Figure 2B:
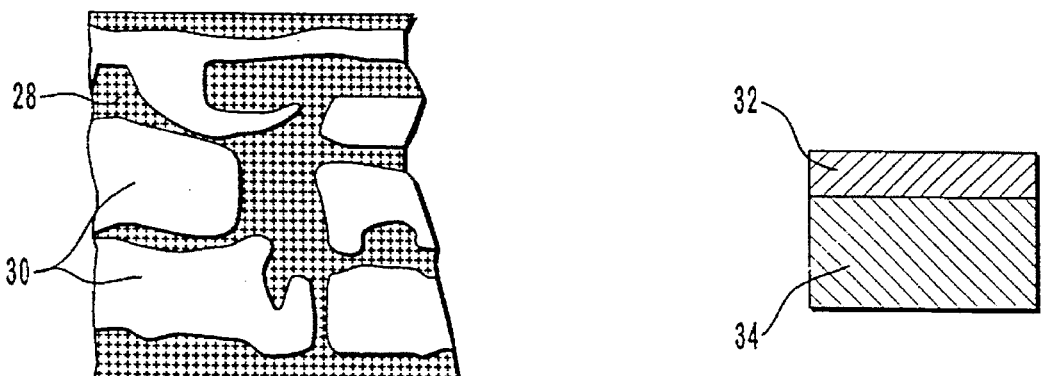
Figure 2C:
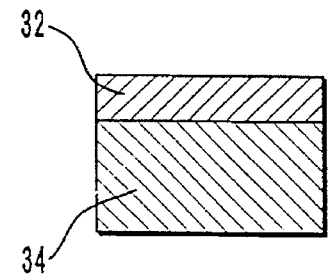
Figure 3B:
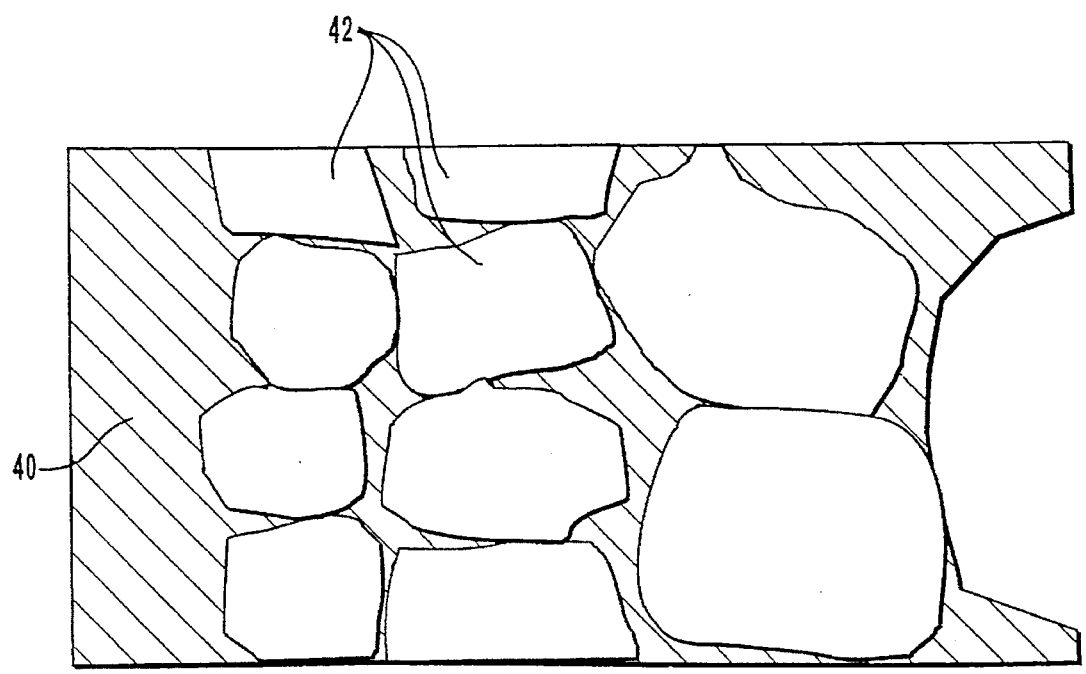
Figure 7A:
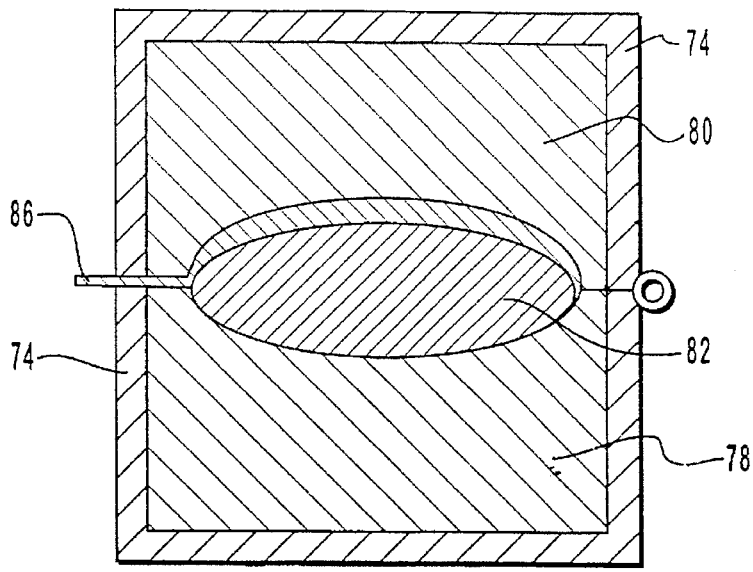
FIGS. 7A, 7B and 7C show cross-sectional views of a mold container with an implant model, a mold container filled with the final product material, and the resulting final product implant, respectively.
Figure 7B:
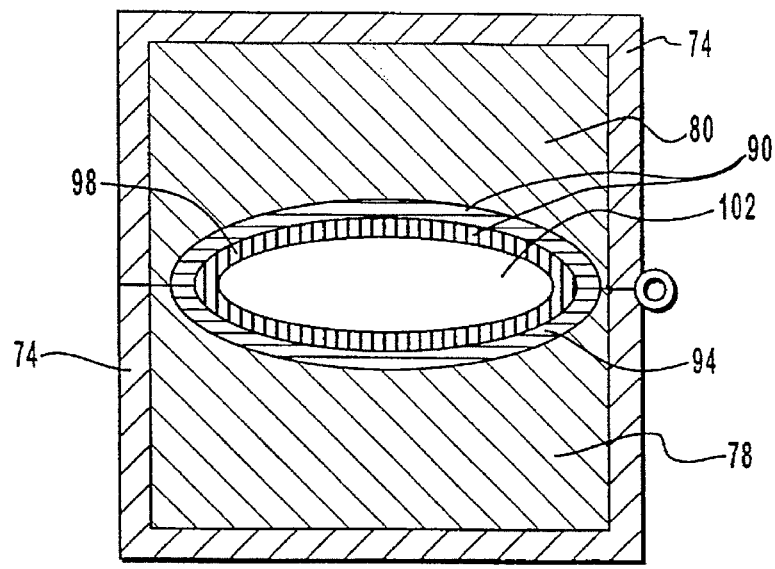
Figure 7C:
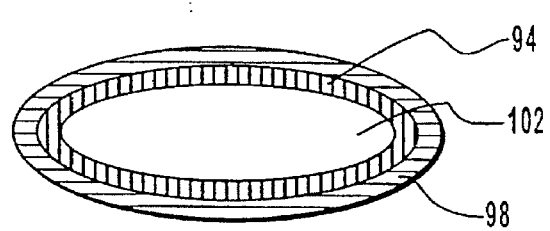
Figure 8A:
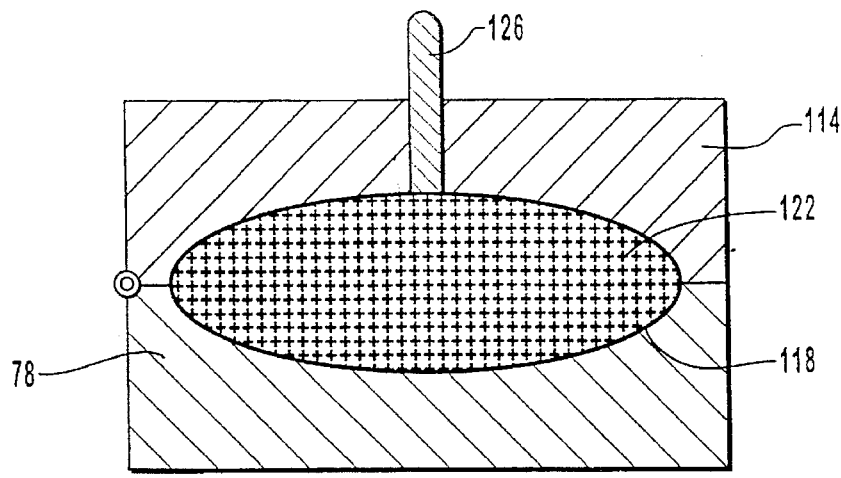
FIGS. 8A, 8B, 8C and 8D show elevational, cross-sectional views of a mold container for constructing a mold form, the mold form with the final product material applied, and two versions of the final prosthesis, respectively, in accordance with the present invention.
Figure 8B:
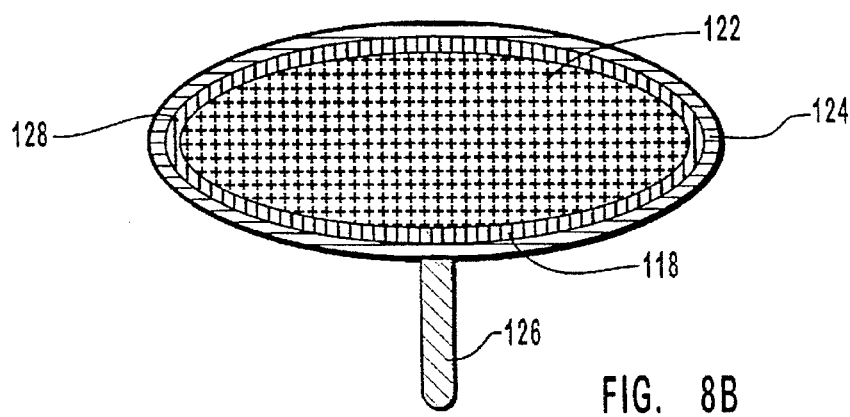

Alternatively, to prepare the SRO-CPMF 122 of FIGS. 8A and 2B, the polymethylmethacrylate model 82 of FIG. 7A affixed with stainless steel handle 126 as in FIG. 8A, may be used by slightly roughening and/or coating the surface of the model with corn syrup to encourage adherence, and then spraying the surface with specific sized sugar particles under air pressure, intimately mixed with a small amount of de-ionized water (in a manner similar to mixing gunite cement). The surface moistened sugar particles, upon striking the model surface 82, adhere to the model and to each other. The thickness of the layer of particles can be controlled to produce a desired thickness sugar SRO-CPMF shell on the outside of the model 82. This sugar shell would then be allowed to dry to form the SRO-CPMF as previously described in FIGS. 8A and 8B.

Figure 8C:
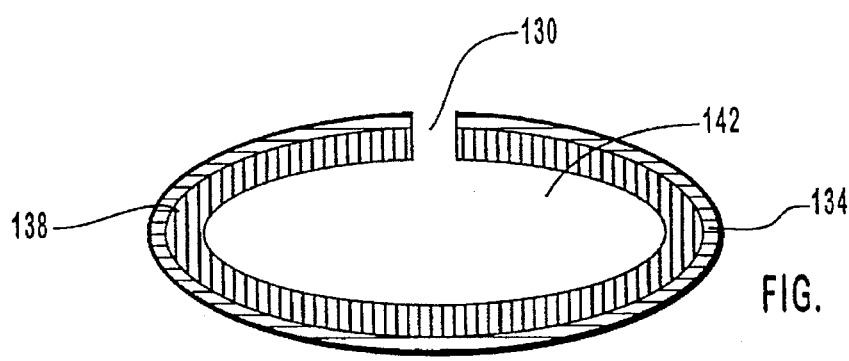
Figure 8D:
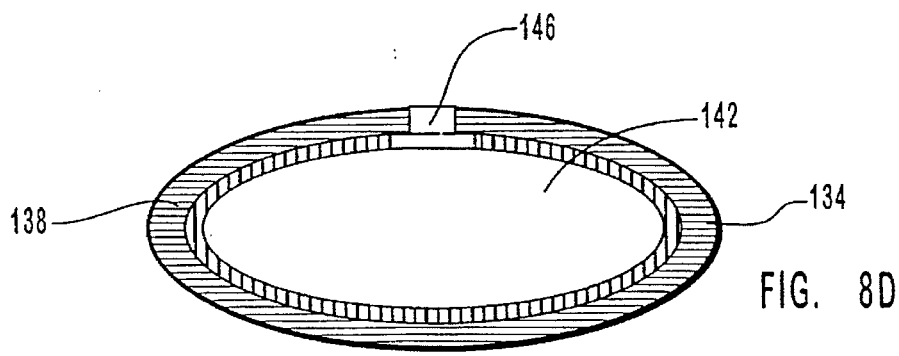

In either example above-described, the mold form is dipped into a medical grade silicone dispersion, by holding onto the handle 126 by hand. Vacuum application to the mold form 122 during or immediately after dipping can increase the depth of penetration of the silicone dispersion and eliminate bubbles and coating irregularities within the mold form. The mold form can be redipped into the silicone dispersion, after drying, from two to six times, depending on the desired thickness of the silicone shell being formed. The first one or two times the mold form 122 is dipped into the dispersion, the silicone flows into the voids in the mold form to develop what will ultimately be the porous portion of the device 138 (FIGS. 8C and 8D). The subsequent dipping of the mold form 122 will simply add nonporous layers 134 (FIGS. 8C and 8D) about the mold form. The thickness of the porous portion in the first example may be controlled by controlling the viscosity of the silicone dispersion and the amount of time and pressure or vacuum application during or shortly after the initial coats, which in turn determines the extent of penetration of dispersion into the mold form 122 and in the second example by controlling the thickness of the SRO-CPMF shell on the polymethylmethacrylate model 82.

After conclusion of the dipping steps, the silicone dispersion is vulcanized in an oven at, for example, 275 degrees F. for about one hour. Then a small (1½ to 2 cm) hole 130 (FIG. 8B) is cut into the nonporous silicone covering around the dipping handle and then hot, de-ionized water is applied to the hole to reach and dissolve the SRO-CPMF material 122. Multiple washings may be required for this. The resulting silicone device consists of a shell whose outer surface 134 (FIG. 8C) is nonporous and whose inner surface 138 is porous. The positions of the nonporous and porous surfaces are reversed, however, by inverting the device through the hole 130 (FIG. 8D) formed to allow entry of hot water to dissolve the mold form 122, so that the porous portion 138 (FIG. 8D) of the device is now on the outside and the nonporous portion 134 (FIG. 8D) is on the inside. Of course, a void or cavity 142 is still present in either device in FIG. 8C or 8D.

To close the hole or opening 130, a small solid silicone patch 146 is glued with a medical grade silicone adhesive (or a patch of unvulcanized silicone rubber is vulcanized) in place over the opening. Of course, the outer patch surface 146 could be made either porous or nonporous depending upon the need. Also, conventional self-sealing valves could be included in the patch 146 so that previously described materials could be inserted into the void 142 at any time.

Figure 9:
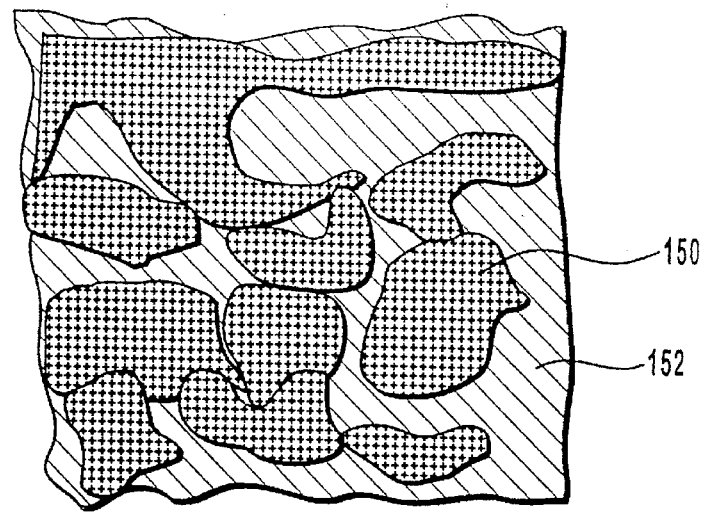
FIG. 9 shows an elevational, cross-sectional and fragmented view of a prosthesis for use as a drug delivery implant.

Another example of the use of the present invention involves utilizing the SRO-CPMF particles 150 (FIG. 9) within the final product material 152 by leaving at least some of the SRO-CPMF material in the final product to be dissolved over time, after implantation of the product in a person's body. In effect, the device becomes a drug delivery system for implantation in which the SRO-CPMF material consists of or includes drugs to be delivered in or on the human body. Examples of such drugs which might be included in a device during fabrication are gentamicin, tetracycline or cephalosporin crystals, but many other drugs available or drugs which can be disposed in crystalline form could also be used. Most drugs such as antibiotics, which are usually supplied in a powder form, would be dissolved and recrystallized into larger crystals. Depending on their inherent stickiness and heat stability, the crystals would then be partially dissolved and mixed and formed as a moldable mass or heated and compacted, to be used as the SRO-CPMF as described for sugar. (A filler medium such as dextrose crystals can be mixed with the drug to get a smaller concentration of drug if needed.) Alternatively, the crystals can be bound together with a neutral, non-drug interacting, biologically compatible binding medium such as a concentrated dextrose solution in a ratio of 1 part saturated dextrose solution to between 4 and 40 parts drug crystal. Still another alternative is to dissolve or suspend the drug particles in powder form in the dextrose solution and then use this solution to coat other particles, such as another drug or dextrose crystals to form a SRO-CPMF with precipitated dextrose and drug particles on the surface. The dissolved or suspended drug within the dextrose solution may also be recrystallized, sized and made into a SRO-CPMF itself as in the previous examples of sugar SRO-CPMF. Specifically, an example of such a combination would be the dissolution of gentamicin crystals in a pharmaceutically pure saturated dextrose (sugar) solution, recrystallization and molding of these particles into a SRO-CPMF into which a silicone or other final product material is then placed.

Differing concentrations of drug in different layers (in the same manner in which graduated sizes of particles are used in making a SRO-CPMF as in FIG. 3B) or different drugs in different layers may be produced within the SRO-CPMF mold material so that a different concentration of a certain drug, or a different drug will be encountered as ingrowth proceeds depending on the mechanism used by the body for removing the selected SRO-CPMF.

As indicated, the drug or drug infiltrated mass may be used as the moldable mass for the SRO-CPMF, and a biologically compatible material such as Medical Grade Silicone Rubber used as the final product material. An RTV (room temperature vulcanizing) silicone is the preferred material for the final product so that the heat required for other forms of silicone won't be needed—such heat polymerization might otherwise denature or alter the active form of the drug. Alternatively, a polyvinyl alcohol or polyglycolic or polylactic acid, or other absorbable final product material, might be used. To insure sterility, the fabrication of the SRO-CPMF is done under sterile conditions (all materials and appliances of fabrication are sterilized and the drug is supplied as sterile), or alternatively, the device is fabricated under "clean room" conditions and the device sterilized by accepted techniques which do not alter the bioactivity of the drug. The device is then implanted in or placed on the human body, or into a body cavity, to allow tissue to grow into or fluids to penetrate, so that the body will passively and/or actively dissolve the SRO-CPMF to cause release of the drug. Again, the prevention of the thick capsule formation and the lack of isolation of the vascularity from the implant, characteristics which can be built into the porous portion of the device with the above-described methods, is an important key to the success of such an implanted device. By controlling the size of the implant, the amount of surface area of porosity exposed for passive dissolution or tissue ingrowth, the size of the pores, the size of the pore interconnections, the concentration of the drug in the SRO-CPMF, the water-soluble versus fat soluble form of the drug, and the site of implantation, control of the pharmacokinetics are made possible. Also, a combined device where drugs are incorporated into both the SRO-CPMF and the final product material resulting in a biphasic adsorption can be made by physically mixing the drug particles or using concentrated drug solutions and mixing them with the final product material and processing them as described above.

Figure 10:
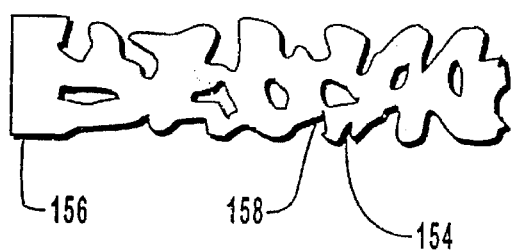
FIG. 10 is a side, cross-sectional view of a porous metal alloy product made in accordance with the present invention.

Another example of the use of the present invention involves production of a porous metal or metallic alloy device 154 (FIG. 10), which in this example includes a nonporous section 156 and a porous section 158, for use in or on the human body as an electrode or battery plate, etc. To produce metallic partially porous devices, the sugar SRO-CPMF is first vacuum-impregnated with wax. The SRO-CPMF is then removed by dissolution and dried. A conventional ceramic refractory material, taking the place of the SRO-CPMF, is then vacuum-impregnated into the wax. The metal, such as silver, gold, Vitallium or other castable metals are then heated to their molten phase and cast into the negative wax replica of the SRO-CPMF made by ceramic refractory material, by standard centrifugal casting techniques taking the place of the wax. This creates the same porous form as would have resulted if silicone rubber had been introduced into the SRO-CPMF as described earlier, but out of metal.

To create ceramic partially porous devices, the SRO-CPMF is vacuum impregnated with wax as above, the SRO-CPMF dissolved, and the wax dried. A concentrated suspension of fine particle-sized (5 mm) ceramic, e.g., α-alumina, is then vibrated into the pores of the wax open-cell porous mold form, and the ceramic is allowed to dry. The combination of the wax mold form and ceramic are then heated to about 400 degrees C. and the wax allowed to melt and/or burn off. The ceramic is then sintered at 1650–1700 degrees C. The porosity this time is the negative replica of the SRO-CPMF, with the sintered ceramic essentially resulting in a duplicate of the SRO-CPMF.

With the above type construction techniques with sugars, waxes, refractories and other selectively removable materials serving as the SRO-CPMF or filling the spaces between the SRO-CPMF, positive or negative copies of the SRO-CPMF can be created. All of the other previously described control techniques as to porous and non-porous portions, size and position of the open-cell surface area, etc. are applicable to producing the metallic or ceramic devices described. These devices, as already mentioned, could be used in a variety of situations where large surface area exposure of the device is desired.

Figure 11:
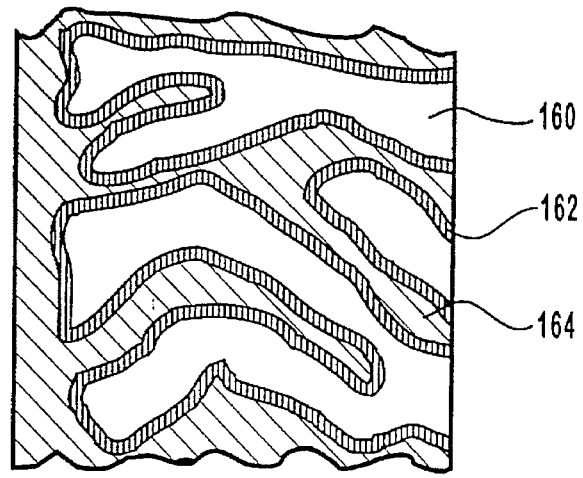
FIG. 11 shows a cross-sectional and fragmented view of a doubly-porous prosthesis, with mold form still in place, made in accordance with the present invention.

Another example of the use of the method of the present invention involves construction of a device as with any of the previous examples but adapted for use as a dialysis device or a blood oxygenation device. These devices utilize a doubly porous membrane such as illustrated in FIG. 11. Mold form material 164 is created as described with any of the above methods. The liquid phase final product material (illustratively RTV silicone rubber) is then forced into the interstices of the mold form 164. Then, most of the silicone rubber is forced out of the interstices of the mold form by a liquid or gas, such as compressed nitrogen gas, leaving the mold form with a very thin coat of the silicone rubber 162. This reproduces the open-celled structure on the side of the silicone rubber coat or membrane, opposite the location of the mold form material—forms a secondary porosity 160 (see FIG. 11). The next step in the process, as described earlier, is to cure or polymerize the silicone rubber 162 and to dissolve out the mold form material 164 creating the primary porosity (where the mold form material was). It is helpful to use some kind of surfactant such as a weak soap solution in both the solution dissolving out the mold form material and on the secondary porosity side to prevent adherence of the silicone rubber to itself which would close off the porosities thus created.

When the dissolution of the mold form material is complete, there remains a doubly porous silicone rubber membrane 162, with no communication between the two porosities. The primary porosity 164 (visualized without the mold form material) on the one side of the membrane 162 has its porosity, created by the mold form, whereas the secondary porosity 160 on the other side of the membrane has its porosity created by removing much of the silicone rubber within the interstices of the mold form. This side of the membrane may then be isolated by standard molding or construction techniques so that a gas, such as oxygen, or a liquid, such as a kidney dialysis solution, can be circulated through this secondary porosity, without cross-circulation into the primary porosity. Such a device may then be implanted so that the primary porosity 164 is filled intimately with new blood vessels and loose connective tissue. It has been found that this device is very tissue-compatible, with no fibrosis developing within the primary portion, and with capillaries and blood vessels literally within close proximity of the silicone rubber membrane.

With the prosthesis described above used as a dialysis device, a standard dialysis solution would be circulated through the secondary porosity 160. The membrane 162 between the porosities 160 and 164 acts like a dialysis membrane in a standard artificial kidney, removing the unwanted ureas, nitrogen compounds and ions, based on the standard diffusion principles. Due to the large surface area of the primary porosity, and the fact that a capsule doesn't form between the neovascularity and the silicone rubber membrane, an implantable dialysis device is now made practical.

Likewise, a similar device may be constructed for use in blood oxygenation. The device would be implanted and a specific oxygen concentration circulated through the secondary porosity 160. This time, with the thin silicone rubber membrane 162 acting as a gas transfer membrane, oxygen is transferred into the capillaries and vessels ingrown in the primary porosity 164 and carbon dioxide is removed from the vessels into the circulating oxygen in the secondary porosity 160. The carbon dioxide is then subsequently removed.

Figure 12:
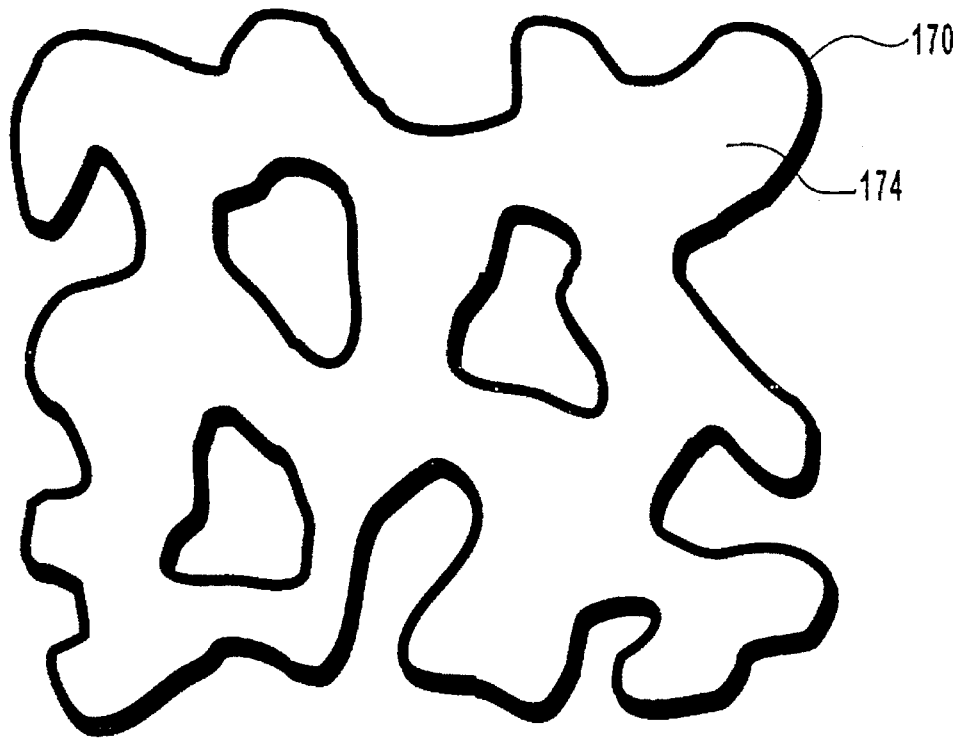
FIG. 12 shows a cross-sectional, fragmented view of a final porous product with a coating of material on the pore surfaces, made in accordance with the principles of the present invention.

Using the previous example, a layered membrane or a final product with a layer coating, such as shown in FIG. 12, may be created as follows. After the thin membrane of the final product of silicon rubber 170 has been applied to the mold form, as in the previous example, and cured, but before the mold form is removed, a secondary material in its liquid form, e.g., a Biomer polyurethane solution 174 is vacuum impregnated into the secondary porosity. This may either be partially blown out as described for forming the membrane in the previous example, or a thin (i.e., 10 to 15 percent) solution of the Biomer may be vacuum impregnated and dried (resulting in removal of the 85 to 90 percent solvent) in an oven at 50 degrees C. for two hours. This leaves a double-layered, interlocking membrane with separate porosity on each side, as shown in FIG. 12.

Similarly, the physical interweaving of two materials processed as above can be used to advantage in joining two dissimilar materials (which do not readily adhere) to each other. This can be done so that there is double porosity left as in the FIG. 12 example. Two other methods can also be used to join the two materials, and give a porous or a nonporous surface on one side. Using the example described for FIG. 11, the thin silicone rubber membrane is applied to the mold form and cured, but the mold form is kept in place. The next material, say a catalyzed polyester resin, is vacuum impregnated into the secondary porosity and allowed to polymerize. The mold form is removed, resulting in a nonporous polyester surface and polyester interlocking structure in intimate contact with the thin silicone membrane, with porosity on the side of the membrane away from the polyester resin.

Figure 13:
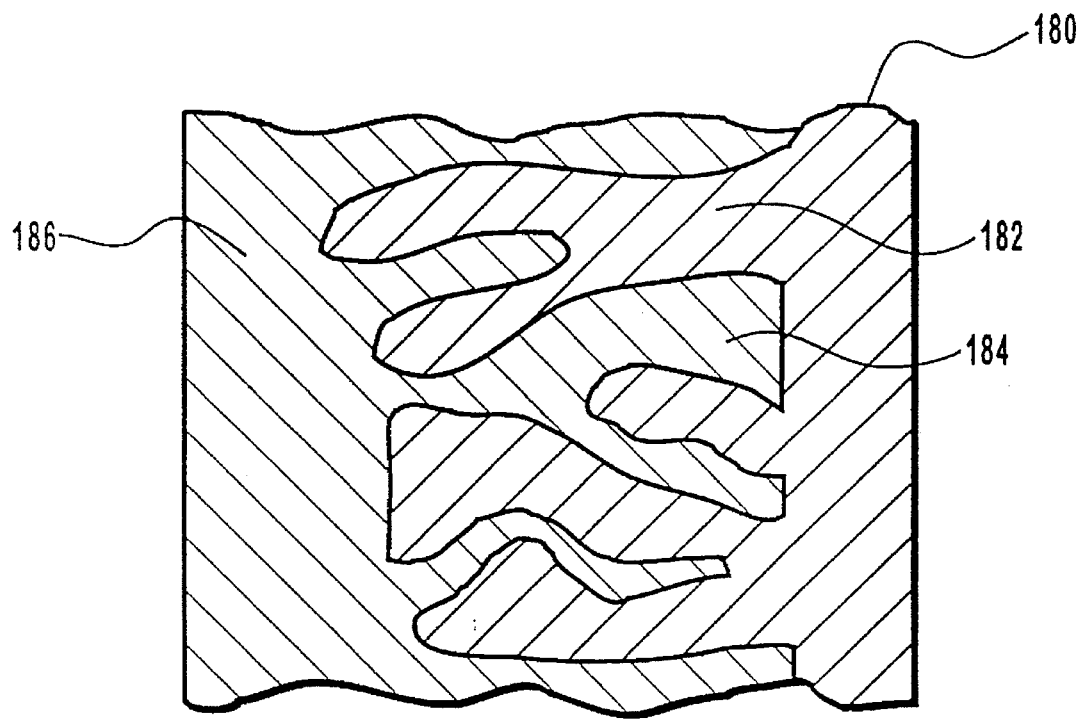
FIG. 13 is a side, cross-sectional, fragmented view of two interlocking materials produced in accordance with the present invention.

In a similar manner, two sheets or structures can be joined utilizing the porosity. This is done by creating a partially porous sheet of silicone rubber, as described in the example accompanying FIG. 6, having a nonporous section 186 (FIG. 13) and a porous section 184. After drying, a catalyzed polyester resin is vacuum impregnated into the porosity of the silicone rubber. After polymerization, the resultant structure has two nonporous surfaces, 186 for the silicone rubber 186, and 180 for the polyester resin, with their associated porosities 184 and 182 respectively being in intimate contact mechanically to interlock the two materials together.

It is to be understood that the above-described arrangements are only illustrative of the application of the principles of the present invention. Numerous modifications and alternative arrangements may be devised by those skilled in the art without departing from the spirit and scope of the and the appended claims are intended to cover such modifications and arrangements.

I claim:

1. A method of forming a selectively removable open-cell porous mold form comprising the steps of:
   (a) obtaining particles having sizes in the range of about 25–600 microns, said particles comprising a material capable of self-adhering when exposed to a first selected condition, solidifying when exposed to a second selected condition, and desolidifying when exposed to a third selected condition;
   (b) exposing said particles to a first selected condition such that the particles adhere into a mass of continuously interconnected particles defining continuously interconnected pores, said pores being each connected to at least one adjacent pore by pore interconnections and said pores and pore interconnections having a substantially smoothly flowing configuration;
   (c) forming said mass of continuously interconnected particles into a predetermined shape; and
   (d) exposing said formed and shaped mass to a second selected condition to solidify said mass into a selectively removable mold form for use in preparing devices having a porous portion corresponding to said continuously interconnected and substantially smoothly flowing pores and pore interconnections.

2. The method of claim 1 wherein the particles obtained in step (a) comprise a material selected from the group consisting of polymers, ceramics, metals, biological derivatives and combinations thereof.

3. The method of claim 1 wherein the particles obtained in step (a) comprise a porous material.

4. The method of claim 1 wherein step (b) comprises the selected condition of adding a liquid to a solid phase of said particles to thereby affect the binding between the particles.

5. The method of claim 4 wherein said solid phase is dissolvable in said liquid such that partial dissolution of said solid phase is achieved.

6. The method of claim 5 wherein the liquid comprises water and the solid phase comprises sugar.

7. The method of claim 5 wherein the liquid comprises saturated sugar solution and the solid phase comprises sugar.

8. The method of claim 4 wherein step (d) comprises the second selected condition of removing the liquid.

9. The method of claim 1 wherein the particles obtained in step (a) are crystals and step (d) comprises the second selected condition of effecting crystallization of said particles.

10. The method of claim 1 wherein step (b) comprises the selected condition of heating a solid phase of said particles to thereby affect the binding between the particles.

11. The method of claim 10 wherein step (d) comprises the second selected condition of cooling of said particles.

12. The method of claim 1 wherein the particles are coated with a selected material, said coating material being capable of self-adhering when exposed to a first selected condition and capable of solidifying when exposed to a second selected condition.

13. The method of claim 12 wherein the particles are coated with sugar.

14. The method of claim 12 wherein the particles are coated with a polymerizable material.

15. The method of claim 14 wherein step (d) comprises the second selected condition of effecting polymerization of said coating.

16. The method of claim 1 comprising the further step of mixing fibers into the particles obtained in step (a) such that portions of fibers extend into the pores and pore interconnections of the solidified mold form.

17. The method of claim 16 wherein the fibers comprise fiberglass or carbon graphite fibers.

18. The method of claim 2 wherein the particles comprise a thermoplastic polymer.

19. The method of claim 18 whereto the thermoplastic polymer is selected from the group consisting of waxes, paraffins, polyethylenes, nylons, polycarbonates, and polystyrenes.

20. The method of claim 1 wherein the particles comprise a pharmaceutical composition.

21. An open-cell porous mold form made by the method of claim 1.

* * * * *

UNITED STATES PATENT AND TRADEMARK OFFICE
CERTIFICATE OF CORRECTION

PATENT NO. : 5,624,674

DATED : April 29, 1997

INVENTOR(S) : William J. Seare, Jr.

It is certified that error appears in the above-identified patent and that said Letters Patent is hereby corrected as shown below:

Column 6, line 26, "15" should read --20--
Column 10, line 48, "used a percutaneous" should read --used as a percutaneous--

Signed and Sealed this

Sixteenth Day of September, 1997

Attest:

BRUCE LEHMAN

Attesting Officer

Commissioner of Patents and Trademarks